United States Patent [19]

Bendel et al.

[11] 4,449,530

[45] May 22, 1984

[54] HEMOSTATIC CLIPS AND METHOD OF MANUFACTURE

[75] Inventors: Lee P. Bendel, Lebanon; Timothy Sardelis, Somerset, both of N.J.

[73] Assignee: Ethicon, Inc., Somerville, N.J.

[21] Appl. No.: 283,692

[22] Filed: Jul. 15, 1981

[51] Int. Cl.³ .................. A61B 17/12; A61B 17/00
[52] U.S. Cl. .................. 128/325; 128/346; 128/326
[58] Field of Search ........... 128/326, 325, 346, 335, 128/334 R, 336

[56] References Cited

U.S. PATENT DOCUMENTS

| | | |
|---|---|---|
| 1,983,969 | 12/1934 | Davis .................. 128/346 |
| 2,757,665 | 8/1956 | Tanikawa .................. 128/346 |
| 3,006,344 | 10/1961 | Vogelfanger .................. 128/326 |
| 3,032,039 | 5/1962 | Beaty .................. 128/346 |
| 3,166,071 | 1/1965 | Mayer .................. 128/346 |
| 3,175,556 | 3/1965 | Wood et al. .................. 128/326 |
| 3,204,636 | 9/1965 | Kariher et al. .................. 128/346 |
| 3,363,628 | 1/1968 | Wood .................. 128/346 |
| 3,766,926 | 10/1973 | Bliss .................. 128/346 |
| 4,091,815 | 5/1978 | Larsen .................. 128/346 |

*Primary Examiner*—C. Fred Rosenbaum
*Assistant Examiner*—C. W. Shedd
*Attorney, Agent, or Firm*—Robert L. Minier

[57] ABSTRACT

Metallic, hemostatic clips providing a reduced gap when closed about a tubular vessel.

6 Claims, 5 Drawing Figures

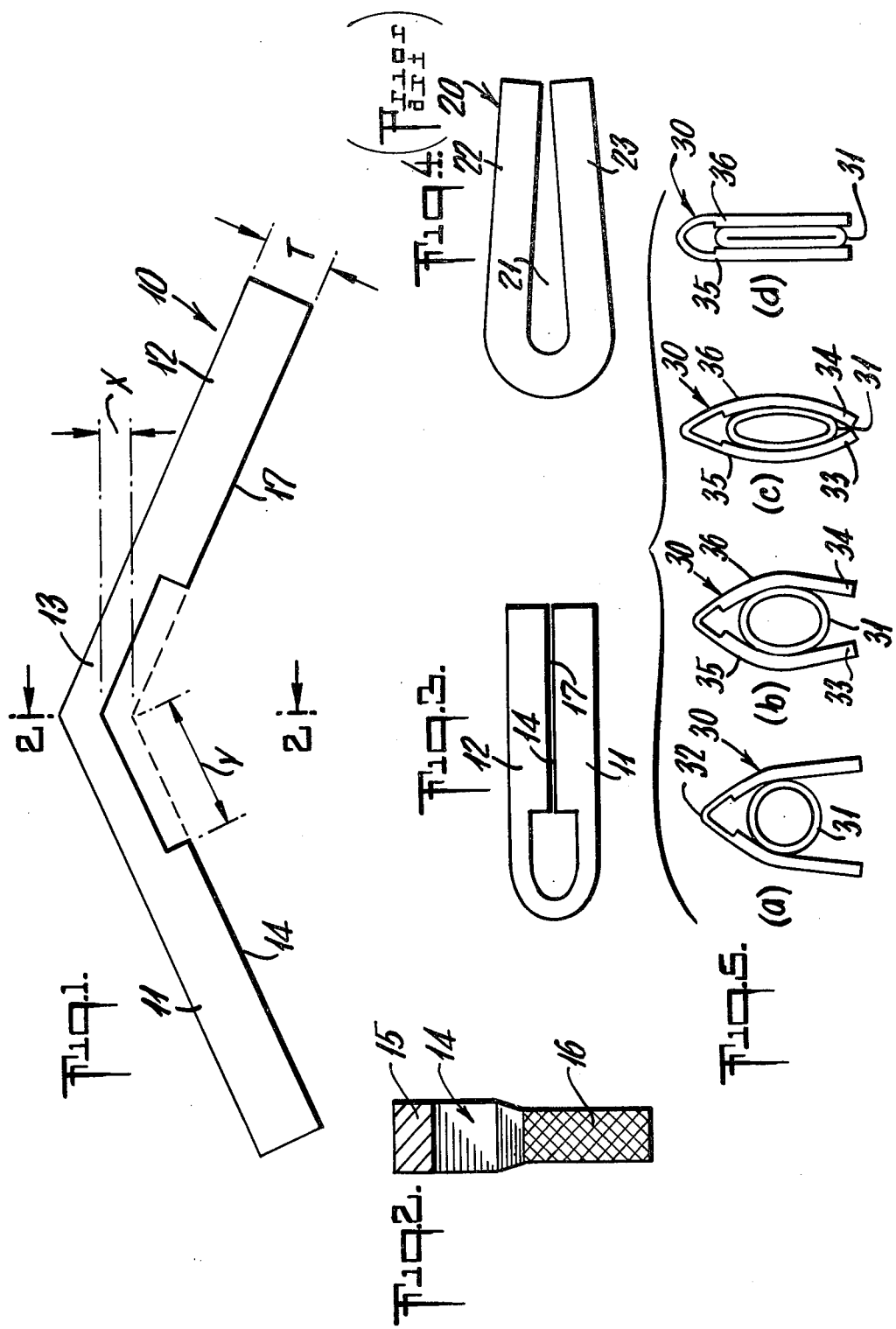

HEMOSTATIC CLIPS AND METHOD OF MANUFACTURE

BACKGROUND OF THE INVENTION

The present invention relates to devices used to close or shut tubular members and, more particularly, to hemostatic clips used to close blood vessels within the body and to methods for manufacturing such hemostatic clips.

During many surgical procedures, the surgeon will have to close or ligate various blood vessels before severing the vessels in order to prevent excessive bleeding and reduce the risk to the patient of blood loss.

A prior technique to close a blood vessel is to ligate it; that is, tie a surgical suture about the vessel to close the vessel. Also, there are various types of metal devices or clips having a pair of legs connected at their proximal ends that can be placed about the vessel and the legs urged or squeezed together to shut the blood vessel. Very often the clip is notched at its proximal end where the legs meet to insure that when the legs are urged together the clip bends at the notch. Hemostatic clips are well known in the prior art and are disclosed in numerous U.S. Patents as, for example, Nos. 3,439,523, 3,270,745, 3,363,628, 3,463,156, 3,439,522, 3,439,523, and 4,146,130.

A serious problem with the prior art hemostatic clips is, though they may be closed about a blood vessel and shut off the flow of blood, there is very often a gap left in the closed clip.

The open clip comprises a pair of leg members connected at their proximal ends with their distal ends spaced apart. The open distal ends of the clip are placed about the vessel to be closed and using a suitable instrument the legs are urged together in an attempt to bring the distal ends in contact and place the legs substantially parallel and in uniform contact with the surface of the vessel. However, in practice the uniform contact is very seldom attained and instead there are spaces or areas of the leg of the clip which are in greater contact with the vessel than other spaces or areas of the clip. The areas with the lesser contact or pressure on the vessel are termed the gap. This gap very often allows the clip to move or slide along the length of the vessel about which it has been closed. When this happens, and the vessel has been cut, in many instances, the clip will slide off the cut end of the blood vessel thus allowing the flow of blood from the now unclosed vessel. The gap in part is caused by the construction of the clip in that the clip is designed so that the distal end of the leg members close first to entrap the vessel in the clip and prevent the vessel from slipping out of the clip on closing the leg members. The leg members are then urged toward each other to close the vessel. The gap is also in part a function of the yield strength of the metal used to form the clip. The higher the yield strength of the metal, the greater the possibility of forming a gap and the greater the size of the formed gap upon closing the clip. As previously mentioned, the gap is usually not sufficient so there is leakage of blood from the severed vessel; however, the gap is often sufficient to allow the clip to slide along the blood vessel. This can often happen when the surgeon or nurse is in the surgical area and is attempting to wipe blood or clean the operative area with a sponge and a corner of the sponge catches on the clip. If the gap is large enough the clip will slide on the vessel even to the point of being removed from the cut end of the vessel.

What we have discovered is an improved clip which has a minimal gap upon closing and, hence, more positively closes the vessel during the surgical procedure. Our new clips are made from metal such as stainless steel, tantalum, and the like.

SUMMARY OF THE PRESENT INVENTION

In accordance with the present invention, our new metal hemostatic clip comprises a pair of leg members connected at their proximal ends by a thinned hinge area. The hinged area is thinned so it is at least 8% thinner then the remaining portion of the leg members. The length of the thinned area is sufficient so as not to interfere or hinder the closing of the clip and to insure that the leg members close at the hinge area. We have found that if the length of the thinned area along each leg member is from about $\frac{1}{2}$ to 3 times, preferably 1 to 2 times the thickness of the leg member, we can insure the leg members will close in the hinged area and we substantially eliminate any hinderance from the hinge area when closing the clip. It is preferred that the thin area of the clip be obtained by coining the desired area. When coining the clip to produce the thin area, the thin area becomes slightly wider and longer and the section modulus of the clip is reduced. Though the thin area may also be produced by machining or the like, such techniques may reduce the section modulus even more than coining; however, in many instances, the clip will still be satisfactory.

The invention will be more fully described and specific embodiments given in the following drawings and description.

BRIEF DESCRIPTION OF THE DRAWINGS

FIG. 1 is a side view of the new metal hemostatic clip of the present invention;

FIG. 2 is a view of the clip depicted in FIG. 1 taken along line 2—2;

FIG. 3 is the new metal hemostatic clip of the present invention in a closed position;

FIG. 4 is a clip of the prior art shown in a closed position; and

FIG. 5 is a 4-step schematic view of the various configurations of a clip as it is being closed about a vessel.

DETAILED DESCRIPTION OF THE DRAWINGS

In FIG. 1 there is shown the clip 10 of the present invention. The clip comprises leg members 11 and 12 which are connected at their proximal end by a thinned hinged area 13. The hinge area is thinned the amount (X) as compared to the remaining portion of the leg member (T). The thinned portion extends a distance (Y) from the apex of the clip to the thickened leg members. In FIG. 2 there is shown the inner surface 14 of the leg member 11 of the clip depicted in FIG. 1. As may be seen, the thinned portion 15 of the leg member is somewhat wider than the remainder of the leg member 16 and the thick and narrower portion of the leg member has a diamond type pattern over its surface to improve the gripping of the vessel by the leg member when the clip is closed.

In FIG. 3, the clip of FIG. 1 is shown in its closed position with the inner surfaces 14 and 17 of the thick leb members 11 and 12 being parallel and adjacent with no gap between the leg members of the clip. Contrasted to this, FIG. 4 shows a prior art clip 20 which has been closed but where there is a substantial gap 21 left between the inner surfaces of the leg members 22 and 23. While the clip shown in FIG. 4 will stop the flow of blood in the vessel, it is relatively easily moved or slid along the blood vessel and can cause severe problems should it accidentially be removed from the cut end of the vessel during the surgical procedure. This sliding and removal can easily happen if the clip gets caught by a sponge or an instrument while the surgeon or nurse is working in the operative area. Contrasted to this, our new clip of the present invention, wherein we have thinned a portion of the area at the apex of the clip, unexpectedly closes with substantially no gap between the leg members thus providing greater security in use and minimizing if not eliminating the possible slippage of the clip during the surgical procedure.

FIG. 5 depicts the various configurations of the metallic clip 30 as it is being placed about a blood vessel 31. In FIG. 5a the clip is in its most open position. In this position, the clip 30 is placed about a blood vessel 31 with the vessel as close to the apex 32 of the clip as possible. In FIG. 5b, the clip is starting to be closed and the distal ends 33 and 34 of the leg members 35 and 36 start to close to entrap the vessel 31. As seen in FIG. 5c, the vessel is locked within the clip so that it cannot be displaced from within the confines of the leg members on the further closing of the clip. FIG. 5d shows the clip in its fully closed position.

We have discovered that our new metal clip with its thinned, hinged area produces a clip which unexpectedly has a greatly reduced gap in use. As previously mentioned the lower the yield strength of the metal in the clip, the less the gap between the leg members when the clip is closed. It is believed that by thinning the hinge area as we have done we have effectively lowered the force required to close the clip, and surprisingly without any detrimental effect on the overall strength of the clip.

The new clips of the present invention are preferably produced by starting with round wire and rolling and embossing the wire to a rectangular cross section. One surface of the wire is embossed in a diamond pattern and this surface will become the inner surfaces of the leg members. The clips are fabricated in what is termed a "4-slide" machine which is well known and used in the industry. The rectangular shaped wire is fed to the machine and the wire bent and coined to form the hinged area and then cut to form individual clips. After the clip has been formed, it is preferred that the clip be annealed to fully soften and give it as low a yield strength as possible.

The notched or hinged area must be thinned at least 8% of its original thickness and preferably from about 11 to 20% of its original thickness. If the area is thinned less than 8%, it is possible that on bending the clip it will not bend at the thinned area but at some area along a leg member and will not entrap the vessel when the clip is closed. If the hinged area is thinned more than about 30% of the original thickness, the clip may be too fragile and may break in manufacture or at the hinge area in use. The length of the thinned area along each leg member should be sufficiently long so as not to interfere with the closing of the clip and insure that the clip upon bending will bend at the hinged area. We have found that a thinned length along each leg member of about 1 to 2 times the thickness of a leg member to be most satisfactory; though thinned lengths of from about ½ to 3 times the thickness of a leg member may also be used. Our new clip may be made out of any of the biologically acceptable metal materials such as tantalum, stainless steel and the like.

The following is a comparative example between the clips of the present invention and prior art clips in which the thickness is uniform along the entire length of the clip with a notch at the center of the clip. Several hundred clips of each type are produced on a standard 4-slide machine. All clips are processed and annealed in the same manner. Ten clip appliers are used to close 6 clips each. As previously described, by gap it is meant there is something less than line to line contact between the inner surfaces of the leg members when the clip is closed, and is measured with an optical comparator and recorded in thousandths of an inch. The gaps of these clips are measured using an optical comparator and are reported in the Table below. The standard clips tested have an average gap of 0.0033 inches. The clips of the present invention, with the clip thinned at the apex and the dimensions of the thinned area being 20% thinner than the leg members of the clip and the length of the thinned area being approximately equal to the thickness of a leg member, have an average gap when tested of 0.0021 inches.

TABLE I

| Applier No. | Prior Art Clips* | Clips of the Present Invention |
|---|---|---|
| 1 | .0044 | .0020 |
| 2** | .0047 | .0032 |
| 3 | .0035 | .0022 |
| 4** | .0040 | .0027 |
| 5 | .0044 | .0024* |
| 6** | .0015 | .0016 |
| 7 | .0022 | .0015 |
| 8 | .0021 | .0013 |
| 9 | .0030 | .0025 |
| 10** | .0035 | .0022 |
| 1018** | .0058 | .0044 |
| AVERAGE | .0033 | .0021 |

*Average of 12 clips, all others are an average of 6 clips
**Appliers used in vitro tests As may be seen from the above Table I, the clips of the present invention unexpectedly have a substantially less gap than the prior art clips.

Four appliers which have a wide span of gaps, plus one applier which was known gave an unacceptable gap are tested in vitro. This test is conducted using veins of the same approximate size as those found in an saphenous vein transplant. Also, arteries of a similar size are isolated and tested. A clip is loaded, numbered and handed to the tester. The clip is applied to the vein or artery and an attempt is made to move it in the axial and longitudinal direction. If the clip is found to be acceptable, a plus mark is recorded next to the test number. If the clip is unacceptable, a negative mark is recorded. Two tests on veins and two tests on arteries are conducted with each of the five appliers. The clips are those of the prior art and the clips of the present invention made as described in the previous example. The following are the results of the tests:

TABLE II

| | Prior Art Clips* | | Clips of the Present Invention | |
|---|---|---|---|---|
| Applier No. | Gap | Secure/Insecure | Gap | Secure/Insecure |
| 6 | .0015 | 4/0 | .0016 | 4/0 |
| 10 | .0035 | 0/5 | .0022 | 5/2 |
| 4 | .0040 | 0/4 | .0027 | 4/0 |

TABLE II-continued

| | Prior Art Clips* | | Clips of the Present Invention | |
|---|---|---|---|---|
| Applier No. | Gap | Secure/Insecure | Gap | Secure/Insecure |
| 2 | .0047 | 0/4 | .0032 | 4/0 |
| 1018 | .0056 | 0/4 | .0044 | 0/4 |

As is readily seen from the above Table II, the clips of the present invention have improved gap characteristics and provide greater security in the ligation or closing of vessels.

Having now described the present invention, it will be readily apparent to those skilled in the art various modifications and alterations may be made to the present invention without departing from the spirit and scope thereof.

What is claimed is:

1. A metal hemostatic clip comprising a pair of leg members connected at their proximal ends by a thinned hinge area, said hinge area being at least from 8% to 30% thinner than the thickness of a leg member and said thinned area being slightly wider than and extending a distance along each leg member from the proximal end thereof towards the distal end thereof a distance of from $\frac{1}{2}$ to 3 times the thickness of a leg member, said distance being such that whereby on closing of the clip, the clip bends in the thinned area and when the clip is closed there is substantially no gap between the leg members.

2. A clip according to claim 1 wherein the hinge section is from about 11% to about 20% thinner than the thickness of a leg member.

3. A clip according to claim 1 or 2 wherein the thinned hinge area extends along each leg member a distance from about 1 to 2 times the thickness of a leg member.

4. A clip according to claim 1, or 2 wherein the clip is a stainless steel clip.

5. A clip according to claim 1, or 2 wherein at least one surface of the leg members has an embossed pattern thereon.

6. A clip according to claim 5 wherein the embossed pattern is a diamond pattern.

* * * * *